(12) United States Patent
Lin et al.

(10) Patent No.: US 7,440,607 B1
(45) Date of Patent: Oct. 21, 2008

(54) OUTLIER SUBSTRATE INSPECTION

(75) Inventors: Jason Z. Lin, Saratoga, CA (US); Hong Chen, San Ramon, CA (US); Evgeni Shifrin, Sunnyvale, CA (US); Ashok V. Kulkarni, San Jose, CA (US); Santosh K. Bhattacharyya, San Jose, CA (US); Wei Zhao, Sunnyvale, CA (US); Chien-Huei Chen, San Jose, CA (US)

(73) Assignee: KLA-Tencor Corporation, San Jose, CA (US)

( * ) Notice: Subject to any disclaimer, the term of this patent is extended or adjusted under 35 U.S.C. 154(b) by 829 days.

(21) Appl. No.: 10/980,499

(22) Filed: Nov. 3, 2004

(51) Int. Cl.
*G06K 9/00* (2006.01)

(52) U.S. Cl. .................................................. 382/149

(58) Field of Classification Search ......... 382/141–149, 382/151, 287, 294; 348/86, 92, 125
See application file for complete search history.

(56) References Cited

U.S. PATENT DOCUMENTS

| | | | |
|---|---|---|---|
| 5,495,535 A * | 2/1996 | Smilansky et al. .......... | 382/145 |
| 6,252,981 B1 * | 6/2001 | Guest et al. ................. | 382/149 |
| 6,336,082 B1 * | 1/2002 | Nguyen et al. .............. | 702/179 |
| 6,512,843 B1 * | 1/2003 | Kuwabara .................... | 382/149 |
| 6,539,106 B1 * | 3/2003 | Gallarda et al. ............. | 382/149 |
| 6,853,744 B2 * | 2/2005 | Mueller et al. .............. | 382/147 |
| 6,876,445 B2 * | 4/2005 | Shibuya et al. ........... | 356/237.2 |
| 6,912,304 B1 * | 6/2005 | Aghajan ..................... | 382/149 |
| 6,937,753 B1 * | 8/2005 | O'Dell et al. ............... | 382/141 |

\* cited by examiner

*Primary Examiner*—Daniel G Mariam
(74) *Attorney, Agent, or Firm*—Luedeka, Neely & Graham, P.C.

(57) ABSTRACT

A method of detecting anomalies in a test image. Test features of pixels within the test image are selected, and reference features of pixels within at least one reference image are also selected. A signal distribution of test features and reference features in a multi-dimensional feature space is created, and stored. Those test features of the test image that do not satisfy a set of criteria for normalcy are selected as candidate points. Those candidate points that are statistical outliers are identified as anomalies. Positions of the anomalies are located using the stored signal distribution within which the defects have been identified as a lookup table.

20 Claims, 1 Drawing Sheet

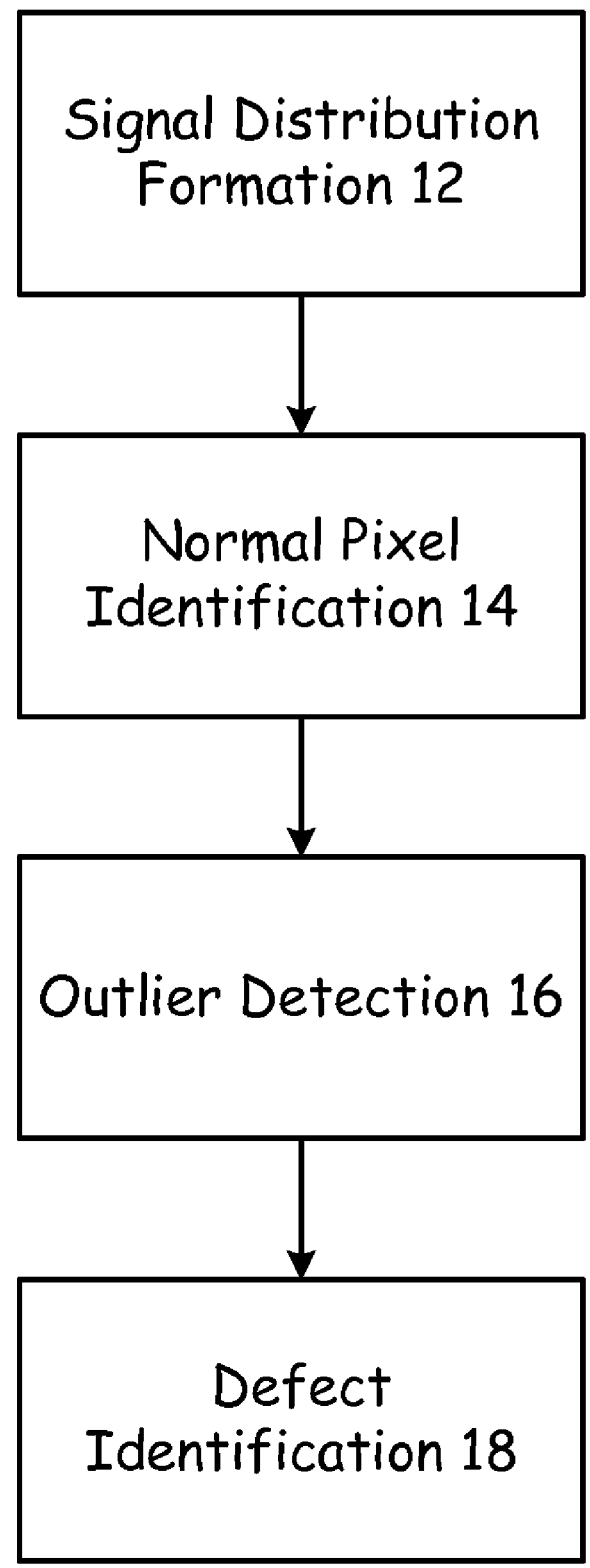

OUTLIER SUBSTRATE INSPECTION

FIELD

This invention relates to the field of integrated circuit fabrication. More particularly, this invention relates to inspection of integrated circuit substrates.

BACKGROUND

Because modern integrated circuits as so small, even the slightest damage or imperfection can potentially destroy the device. Therefore, integrated circuits are rigorously inspected for defects, so as to quickly find and eliminate the sources of such before a great amount of damage is done.

As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

Conventionally, defects in integrated circuits are detected during a substrate inspection by forming optical or other types of images of two adjacent, identical integrated circuits, arrays, or fields of view, and then subtracting the image of one die or cell from the image of the other die or cell. After the subtraction, at least one threshold is used to determine if there is a significant mismatch between the corresponding pixels of the two images, as determined by the subtraction image, which mismatch is indicative of a defect on at least one of the dice.

As the integrated circuit substrate processing gets more and more complicated, the conventional defect detection methods become less and less effective, because of the process variation and substrate noise that exhibit severe color variation and grains on the images collected from the devices on the substrate.

What is needed, therefore, is a system which overcomes, at least in part, at least some of the problems described above.

SUMMARY

The above and other needs are met by a method of detecting anomalies in a test image. Test features of pixels within the test image are selected, and reference features of pixels within at least one reference image are also selected. A signal distribution of test features and reference features in a multi-dimensional feature space is created, and stored. Those test features of the test image that do not satisfy a set of criteria for normalcy are selected as candidate points. Those candidate points that are statistical outliers are identified as anomalies. Positions of the anomalies are located using the stored signal distribution within which the defects have been identified as a lookup table.

In this manner, pixels are grouped to determine the features that are compared. This tends to provide a higher level of distinction between features than that as provided by individual pixel comparison. The manner in which the pixels are grouped to select the features is preferably variable, depending upon many factors, such as which grouping algorithm will tend to enhance the distinction of real defects in the test images.

In various embodiments according to this aspect of the invention, the test image and the at least one reference image each cover multiple dice. In some embodiments, the test features and reference features each include information from more than one pixel, and may each include computed information from more than one pixel. Some embodiments include one or more of compensating for alignment errors, compensating for gray level, and compensating for focus prior to selecting the reference features. The test image and at least one reference image are acquired with different image acquisition modalities in some embodiments. The set of criteria for normalcy may variously include comparing the test features to a distribution of test features, comparing the test features to a reference value, and proximity of a given one of the test features to others of the test features.

BRIEF DESCRIPTION OF THE DRAWINGS

Further advantages of the invention are apparent by reference to the detailed description when considered in conjunction with the FIGURE, which depicts a flow-chart for a method according to an embodiment of the present invention.

DETAILED DESCRIPTION

The various embodiments of the present invention overcome the drawbacks of the conventional defect detection method, and provide a method of substrate inspection with improved sensitivity and robustness. The preferred methods of defect detection according to the present invention can generally be divided into four stages, as depicted in flow-chart 10 of the FIGURE. The first stage 12 is signal distribution formation, the second stage 14 is normal pixel identification, the third stage 16 is outlier detection and the last stage 18 is defect identification.

According to the preferred embodiments of the present invention, images from at least two dice are used to do defect detection. The image associated with the die in which defects are to be detected is called the test image, and the images associated with other dice are called reference images. Similarly, images from at least two array cells are preferably used to detect defects. In general, large numbers of cells in a frame area are processed at the same time to provide adequate statistical information, because an array cell typically has a lesser number of pixels. The following embodiments describe multiple dice defect detection to describe the invention. The extension to multiple cell defect detection, although not explicitly described, logically follows according to the same principles as described herein.

Signal Distribution Formation

In the first stage, signal distribution in a multi-dimensional feature space is first formed, preferably based on test features and reference features extracted from the test images and reference images. A reference feature is defined as some property associated with a same pixel location on multiple reference images. The reference feature can be the average or median gray levels across multiple reference dice at the pixel location. It can also be the range or deviation of the gray levels across multiple reference dice at the pixel location.

The reference feature derived from a pixel location may also include the information around the pixel location. For example, the local range or local average of a three pixel wide by three pixel high area centered at the pixel location on each reference image can be calculated first, and then these local ranges or averages can be used to derive the reference feature of the pixel location. A median of local averages across multiple dice can be one of the reference features of the pixel location. Many other features can be derived according to this principle.

A test feature is preferably derived from a pixel location on the test image as well as the multiple reference images. One example of a test feature is the difference between the gray level on the test image and the average of the gray levels on the reference images. Another example is the difference between the gray level on the test image and the median of the gray levels on the reference images. Similar to the reference features, a test feature derived from a pixel location may also include the information around the pixel location. For example, a local average around a three pixel wide by three pixel high area centered at the pixel location may be used for computing the difference to the average of the local averages around a three pixel wide by three pixel high area of the corresponding location on the multiple reference images.

The images are preferably divided into a number of frames. Each frame preferably covers a significant number of pixels in a local area of a die. For example, 512×512 or 1 k×1 k pixels may form a frame. A multi-dimensional signal distribution is preferably formed based on the test and reference features of the pixels within the frame area, as derived from the test image and at least one reference image. The values of these features are preferably used to identify a point where this pixel should be located in the multi-dimensional feature space. Each point in the multi-dimensional feature space is preferably assigned with a population value. For example, if there are one hundred pixels in the frame area having identical test and reference features, the population value of the feature point is assigned as one hundred.

There may be alignment errors between images that are acquired from multiple dice. In the first stage, image alignment may be performed to remove the offset between images. Furthermore, for a variety of factors such as substrate process variation, system focus error, and other noise, the images acquired from multiple dice may have different background levels or edge sharpness. Traditional filtering operations may be used to compensate for these differences before the images are used to extract the test or reference features. For example, a histogram matching technique may be used to adjust the background gray level or contrast of the images from multiple dice. A high pass or low pass filter may be used to sharpen or blur an image.

As more reference features are used, the computation required also become more extensive. To reduce the complexity, combinations of features can be used to reduce the computation. For example, a linear combination of a reference feature derived from the median of multi-die local gray levels and a reference feature derived from the deviation of multi-die local gray level ranges may form a reference feature. Furthermore, eigenvectors of multiple reference features in the N-dimensional space may be used to reduce the redundancy of information contained in the reference features.

According to another embodiment of the invention, the images acquired for each die may be from multiple channels, each representing different image acquisition modality. For example, both dark field and bright field images may be acquired, and test or reference features extracted from both of them. In another example, scatterings of dark field signals in different orientations may be collected as images of separate channels, and features are extracted from them.

In addition, a test or reference feature can be an advanced feature, which is the correlation coefficient of the test or reference images against an image patch serving as a template.

Normal Pixel Identification

The second stage of the detection method is preferably to identify the pixels that appear to fall into the normal distribution of the pixels within the frame area. According to this invention, there are preferably several valid approaches for defining the normal distribution of the pixels within the frame area.

One approach to identify the normal distribution as based on the population in the local neighborhood of a point location of the signal distribution formed in the multi dimensional feature space in the first stage. For a two dimensional example, a pre-defined population density threshold for the total population of points within, say, a five pixel wide by five pixel high square area in the two dimensional signal distribution may be used as a threshold to determine if a given point in the signal distribution is normal or not. If the population value is greater than the population density threshold, the point is considered normal.

Another approach for identifying the normal distribution is based on the connectedness among points in the signal distribution. For a two dimensional example, a point may be considered normal if, in the signal distribution, there are other points within a pre-defined distance.

Many other approaches may also be used to define the normal distribution. As an example, a point may be considered normal if it satisfies both criteria described above. In principle, if there are a considerable number of pixels that have identical or similar features, they are considered normal and not defective.

Outlier Detection

The third stage of the defect detection method is to identify the pixels that are statistical outliers, which preferably indicate defects on the test substrate. As described above, in the second stage the normal distribution of points of the signal distribution in the multi-dimensional feature space has been identified. Every point that is not identified as normal in the signal distribution is called a candidate point. A candidate point may contain a pixel that is a real defect.

In order to allow some margin for error, a tolerance range is preferably allowed before a point is declared defective. There are also many approaches in defining the tolerance range. One approach is a fixed tolerance range. In a two dimensional example, the tolerance range can be a pre-defined distance from a normal point to the candidate point. If the candidate point is disposed at a greater distant from any normal point than the pre-defined distance, it is declared a defective point. More complex rules such as making the pre-defined distance a function of the reference features can also be added in defining the tolerance range. As an example, the distance may be a function of a reference feature that is defined as the average gray level across multiple reference dice.

The outlier detection in the multi-dimensional feature space can also be accomplished in a number of feature spaces with reduced dimensions, and the final outlier result is then preferably formed by some weighted average of the outliers detected from each reduced dimensional space. Other voting schemes may also be used to select or combine the outliers from the reduced dimensional space.

Preferably, to achieve optimal performance in identifying real defects and eliminating nuisances, parameters such as the tolerance range are tuned. Conceptually, each defective point can be viewed in the multi-dimensional feature space, and the tolerance range is tuned to capture points corresponding to defects of interest, while the points corresponding to nuisances are eliminated. However, visualization of features in the multi-dimension is difficult. The multi-dimensional feature space can be projected into a two or three dimensional feature space for viewing and tuning the tolerance ranges in the projected feature spaces. The detectability of defects in each projection can also be compared, to determine which projection has the best sensitivity or stability to detect defects of interest.

Defect Identification

According to the present invention, defective points are preferably found in the signal distribution during the third stage. It is noted that in the multi-dimensional feature space, each point represents pixels that have certain test and reference features. However, the actual pixel location where the pixel is in the frame area is not retained in the signal distribution. Therefore, it is necessary to identify the defect pixel location.

From the description of stage 1, it is understood that if a pixel falls into a defective point, the pixel is defective. The test and reference images are preferably processed again to determine the test and reference features, and to again identify the pixel locations. The processing is similar to that of the first stage of forming the signal distribution. However, instead of forming the signal distribution, defective pixels are located using the signal distribution within which defective points have been identified as a lookup table. Preferably, the test and reference features computed in the first stage are stored and reused to identify the defect pixel locations in the fourth stage.

Once the locations of the defective points have been identified, they are flagged and reported, such as to the tool operator or in an engineering database, so that an investigation of the defects can be made. In other embodiments, the tool in which the present method of defect detection is implemented also includes methods for defect analysis and identification. In other embodiments the two functions of detection and analysis are separately implemented.

Thus, the embodiments of the present invention have several defining characteristics, as next given. Defect detection using at least one test feature and at least one reference feature are computed from multiple dice or array of cells in a multi-dimensional feature space. Both test and reference features may include local neighborhood information. Test and reference features can be combinations of test or reference features. Test and reference features can be eigenvalues in the multi-dimensional feature space. Test and reference features can be derived from different image acquisition modality. Multiple die images may be aligned and color compensated before features are extracted. Outliers can be detected based on point population in the signal distribution formed in the multi-dimensional feature space. Outliers can be detected based on point connectedness in the signal distribution formed in the multi-dimensional feature space. Outliers can be a weighted combination of outliers detected from feature spaces with reduced dimensions. Detection parameters can be tuned by projecting multi-dimensional feature space into a feature space of reduced dimensions.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of detecting anomalies in a test image, the method comprising the steps of:
   selecting test features of pixels within the test image,
   selecting reference features of pixels within more than one reference image, where the reference images have different modalities,
   creating a signal distribution of test features and reference features in a multi-dimensional feature space,
   storing the signal distribution of the test features and reference features,
   selecting as candidate points those test features of the test image that do not satisfy a set of criteria for normalcy,
   identifying as anomalies those candidate points that are statistical outliers, and
   locating positions of the anomalies using the stored signal distribution within which the defects have been identified as a lookup table.

2. The method of claim 1, wherein the test image and the more than one reference image each cover at least one of multiple dice and multiple cells.

3. The method of claim 1, wherein the test features and reference features each include information from more than one pixel.

4. The method of claim 1, wherein the test features and the reference features each include computed information from more than one pixel.

5. The method of claim 1, further comprising compensating for alignment errors prior to selecting the reference features.

6. The method of claim 1, further comprising compensating for gray level prior to selecting the reference features.

7. The method of claim 1, further comprising compensating for focus prior to selecting the reference features.

8. The method of claim 1, wherein the test image and the more than one reference image are acquired with different image acquisition modalities.

9. The method of claim 1, wherein the set of criteria for normalcy includes comparing the test features to a distribution of test features.

10. The method of claim 1, wherein the set of criteria for normalcy includes comparing the test features to a reference value.

11. The method of claim 1, wherein the set of criteria for normalcy includes proximity of a given one of the test features to others of the test features.

12. A method of detecting anomalies in a test image covering multiple dice of a substrate, the method comprising the steps of:
   selecting test features of computed information from more than one pixel within the test image,
   selecting reference features of computed information from more than one pixel within more than one reference image covering multiple dice, where the reference images have different modalities,
   creating a signal distribution of test features and reference features in a multi-dimensional feature space,
   storing the signal distribution of the test features and reference features, selecting as candidate points those test features of the test image that do not satisfy a set of criteria for normalcy, identifying as anomalies those candidate points that are statistical outliers, and locating positions of the anomalies using the stored signal distribution within which the defects have been identified as a lookup table.

13. The method of claim 12, further comprising compensating for alignment errors prior to selecting the reference features.

14. The method of claim 12, further comprising compensating for gray level prior to selecting the reference features.

15. The method of claim 12, further comprising compensating for focus prior to selecting the reference features.

16. A method of detecting anomalies in a test image, the method comprising the steps of:

selecting test features of pixels within the test image, selecting reference features of pixels within more than one reference image, where the reference images have different modalities, compensating for gray level between the test image and the more than one reference image, compensating for alignment errors between the more than one reference image, creating a signal distribution of test features and reference features in a multi-dimensional feature space, storing the signal distribution of the test features and reference features, selecting as candidate points those test features of the test image that do not satisfy a set of criteria for normalcy, identifying as anomalies those candidate points that are statistical outliers, and locating positions of the anomalies using the stored signal distribution within which the defects have been identified as a lookup table.

17. The method of claim 16, wherein the test image and the more than one reference image each cover multiple dice.

18. The method of claim 16, wherein the test features and reference features each include information from more than one pixel.

19. The method of claim 16, wherein the set of criteria for normalcy includes comparing the test features to a distribution of test features.

20. A method of detecting anomalies in a test image of multiple dice, the method comprising the steps of:

selecting test features of more than one pixel each within the test image, selecting reference features of more than one pixel each within more than one reference image of multiple dice, where the reference images have different modalities, compensating for gray level between the test image and the more than one reference image, compensating for alignment errors between the more than one reference image, compensating for focus differences between the more than one reference image, creating a signal distribution of test features and reference features in a multi-dimensional feature space, storing the signal distribution of the test features and reference features, selecting as candidate points those test features of the test image that do not satisfy a set of criteria for normalcy, identifying as anomalies those candidate points that are statistical outliers, and locating positions of the anomalies using the stored signal distribution within which the defects have been identified as a lookup table.

\* \* \* \* \*